(12) United States Patent
Lindgren et al.

(10) Patent No.: US 6,802,227 B2
(45) Date of Patent: *Oct. 12, 2004

(54) METHOD AND APPARATUS FOR OPTIMIZED SAMPLING OF VOLATILIZABLE TARGET SUBSTANCES

(75) Inventors: Eric R. Lindgren, Albuquerque, NM (US); James M. Phelan, Bosque Farms, NM (US)

(73) Assignee: Sandia Corporation, Albuquerque, NM (US)

( * ) Notice: Subject to any disclaimer, the term of this patent is extended or adjusted under 35 U.S.C. 154(b) by 106 days.

This patent is subject to a terminal disclaimer.

(21) Appl. No.: 10/025,510

(22) Filed: Dec. 19, 2001

(65) Prior Publication Data

US 2002/0134173 A1 Sep. 26, 2002

Related U.S. Application Data

(62) Division of application No. 09/491,115, filed on Jan. 25, 2000, now Pat. No. 6,405,608.

(51) Int. Cl.[7] .................................................. G01N 1/00
(52) U.S. Cl. .................................................... 73/863.12
(58) Field of Search ........................ 73/863.11, 863.12, 73/863.21, 864.73, 864.74; 96/108, 154, 227–229

(56) References Cited

U.S. PATENT DOCUMENTS 2,284,147 A * 5/1942 Herrick .................... 73/864.73
2,386,832 A * 10/1945 Zaikowsky et al. ...... 73/864.74
4,759,210 A * 7/1988 Wohltjen
5,288,310 A * 2/1994 Peters et al.
5,691,206 A * 11/1997 Pawliszyn ................. 73/863.21

OTHER PUBLICATIONS

"Solid–Phase Microextraction", Z. Zhang, M.J. Yand and J. Pawliszyn, Anal. Chem., 66(17), 844A–853A, Sep. 1994.*

* cited by examiner

Primary Examiner—Robert Raevis
(74) Attorney, Agent, or Firm—Russell D. Elliott

(57) ABSTRACT

An apparatus for capturing, from gases such as soil gas, target analytes. Target analytes may include emanations from explosive materials or from residues of explosive materials. The apparatus employs principles of sorption common to solid phase microextraction, and is best used in conjunction with analysis means such as a gas chromatograph. To sorb target analytes, the apparatus functions using various sorptive structures to capture target analyte. Depending upon the embodiment, those structures may include a capillary tube including an interior surface on which sorptive material (similar to that on the surface of a SPME fiber) is supported (along with means for moving gases through the capillary tube so that the gases come into close proximity to the sorptive material). In one disclosed embodiment, at least one such sorptive structure is associated with an enclosure including an opening in communication with the surface of a soil region potentially contaminated with buried explosive material such as unexploded ordnance. Emanations from explosive materials can pass into and accumulate in the enclosure where they are sorbed by the sorptive structures. Also disclosed is the use of heating means such as microwave horns to drive target analytes into the soil gas from solid and liquid phase components of the soil.

9 Claims, 1 Drawing Sheet

METHOD AND APPARATUS FOR OPTIMIZED SAMPLING OF VOLATILIZABLE TARGET SUBSTANCES

This is a division of application Ser. No. 09/491,115 filed Jan. 25, 2000 now U.S. Pat. No. 6,405,608.

This invention was made with Government support under Contract DE-AC04-94AL85000 awarded by the U.S. Department of Energy. The Government has certain rights in the invention.

BACKGROUND OF THE INVENTION

1. Field of the Invention (Technical Field)

This invention relates generally to the field of sampling target analytes in which the target analytes, themselves, are in vapor phase. More specifically, the invention relates to using solid-phase microextraction in sampling of target analytes present in low concentration in a carrier gas, especially where the target analytes, such as emanations from explosive materials, are present in a matrix, such as soil, which comprises gas, liquid and solid components.

2. Background Art

The world faces the growing problem of locating and remediating hidden explosives hazards such as buried land mines and abandoned unexploded ordnance in soil. An approach to the problem that has met with some noted success, and that holds the promise of future improvement, involves chemical sampling of gaseous emanations from explosive materials such as TNT in soil. These emanations may include molecules of the actual hidden explosive substances that penetrate and partition into soil gases or they may include other identifier or marker molecules that can be linked to the presence of explosives in the soil. Examples of such identifier or marker molecules may include chemical breakdown products or manufacturing impurities of the explosive materials of concern.

Challenges exist relating to detection and measurement of target analytes in this context. These challenges stem primarily from the extremely low concentration of explosive molecules or other marker substances typically present in soil gas. Sometimes such concentrations are below the level of parts per billion. Low concentrations can result in problems of long sampling times necessary to collect enough target analyte for accurate detection and/or quantitation. Therefore, strategies are needed for optimizing the collection of the explosive components or other target analytes so that sensitivity of detection is maximized and sampling time is minimized.

For purposes of this disclosure, detection of explosive substances is but one embodiment wherein the principles of the invention can be successfully applied. The methods and apparatuses described and claimed herein can be adapted and applied beneficially to a broad range of chemical sampling challenges wherein low concentration of target analyte makes accurate detection and quantitation difficult.

Solid-phase microextraction (SPME) techniques have been the subject of considerable study in recent years, and SPME is emerging as a favored method for sampling of low concentration explosives and other analytes. References describing SPME techniques, specifically as regards to explosives detection include "Trace Analysis of Explosives in Seawater Using Solid-Phase Microextraction and Gas Chromatography/Ion Trap Mass Spectrometry", S. A. Barshick and W. H. Griest, *Anal. Chem.* 1998, 70, 3015–3020; "Trace Explosives Signatures from World War II Unexploded Undersea Ordnance", M. R. Darrach, A. Chujian, and G. A. Plett, *Environ. Sci, Technol.* 1998, 32, 1354–1358; "Application of Solid-Phase Microextraction to the Recovery of Organic Explosives", K. P. Kirkbride, G. Klass and P. E. Pigou, *J. Forensic Sci.*, 1998, 43(1), 76–81. Each of the references cited above describes generally the use of SPME fibers. Typically, such fibers are fine (~0.25 mm OD) silica fibers coated with a thin layer of a sorbing material. SPME fibers are often coated with a sorbent chosen or engineered to have a high propensity to sorb certain analytes of interest. The fibers are exposed to a gaseous or liquid environment from which a target analyte sample is to be extracted. In general, low (near ambient) temperatures are required for optimal sorption of explosive gases from air.

After a sample is collected, the fiber can then be conveniently inserted into a gas chromatograph (GC) by placing the fiber into the inlet of a GC apparatus. One common way to accomplish this is to use a needle to puncture a septum covering the GC inlet, and a syringe plunger to push the fiber (containing sorbed analytes) through the needle into the GC apparatus. Next, the fiber is rapidly heated to drive off the analytes sorbed to the sorbent substance coating the fiber. The analytes are then swept into the GC column for normal separation and quantitation.

Typically, SPME sampling involves placing the SPME fiber in the headspace above a contaminated or potentially contaminated test subject material (for example, soil). Analytes then passively diffuse through the headspace and some ultimately adhere to the fiber. For gaseous samples of low concentration (such as in the case with explosives in soil gases), diffusion of the analytes through the gas to the SPME fiber can be a rate limiting step, resulting in long sampling times. This is especially true for instances wherein it is necessary for equilibrium to be reached, as is the case, frequently, in quantitation studies. "Solid-Phase Microextraction", Z. Zhang, M. J. Yang and J. Pawliszyn, *Anal. Chem.* 1994, 66(17), 844A–853A; "Headspace Solid-Phase Microextraction", Z. Zhang and J. Pawliszyn, *Anal. Chem.* 1993, 65, 1843–1853.

SPME has been shown to successfully collect target analytes in low concentration in gases and liquids. An opportunity, however, exists for optimization of SPME techniques, and further, a need remains for an optimized method and apparatus for extracting target analyte substances from volumes of gases containing those substances in low concentration. The need is especially apparent as regards to overcoming problems associated with slow equilibration and long sample times.

It is noted that the assignee of this application, at the time the present application is made, also has a separate patent application (Ser. No. 09/205,158, Chambers, et al.) pending before the USPTO pertaining to a different use of chemical sorption in the context of detecting buried munitions. It is submitted, however, that the technology described and claimed in that application is distinct from the novel SPME techniques and apparatuses of the present disclosure, both in terms of theoretical principles and application.

SUMMARY OF THE INVENTION

The present invention provides a method and apparatus for sampling target analytes in which the target analytes, themselves, are in vapor phase or are suspended in a gas, as in the case of emanations from explosive materials present in soil. In one aspect, the invention uses a novel technique of solid-phase microextraction wherein traditional SPME fibers are omitted in favor of using a new SPME capillary. This technique is augmented in one described embodiment by using heating means (for example, microwave heating) to increase gas partitioning where analyte may be present either in gas and liquid, gas and solid, or gas, liquid and solid components present within the matrix to be analyzed. In another aspect, the invention utilizes the heating (such as microwave heating) to increase gas partitioning to enhance sample collection even where traditional SPME fibers are used.

Advantages and novel features will become apparent to those skilled in the art upon examination of the following description or may be learned by practice of the invention. The objects and advantages of the invention may be realized and attained by means of the instrumentalities and combinations particularly pointed out in the appended claims.

DESCRIPTION OF THE FIGURES

The accompanying drawing, which is incorporated into and forms part of the specification, illustrates embodiments of the invention and, together with the description, serves to explain the principles of the invention.

DETAILED DESCRIPTION OF THE INVENTION

Figure 1:
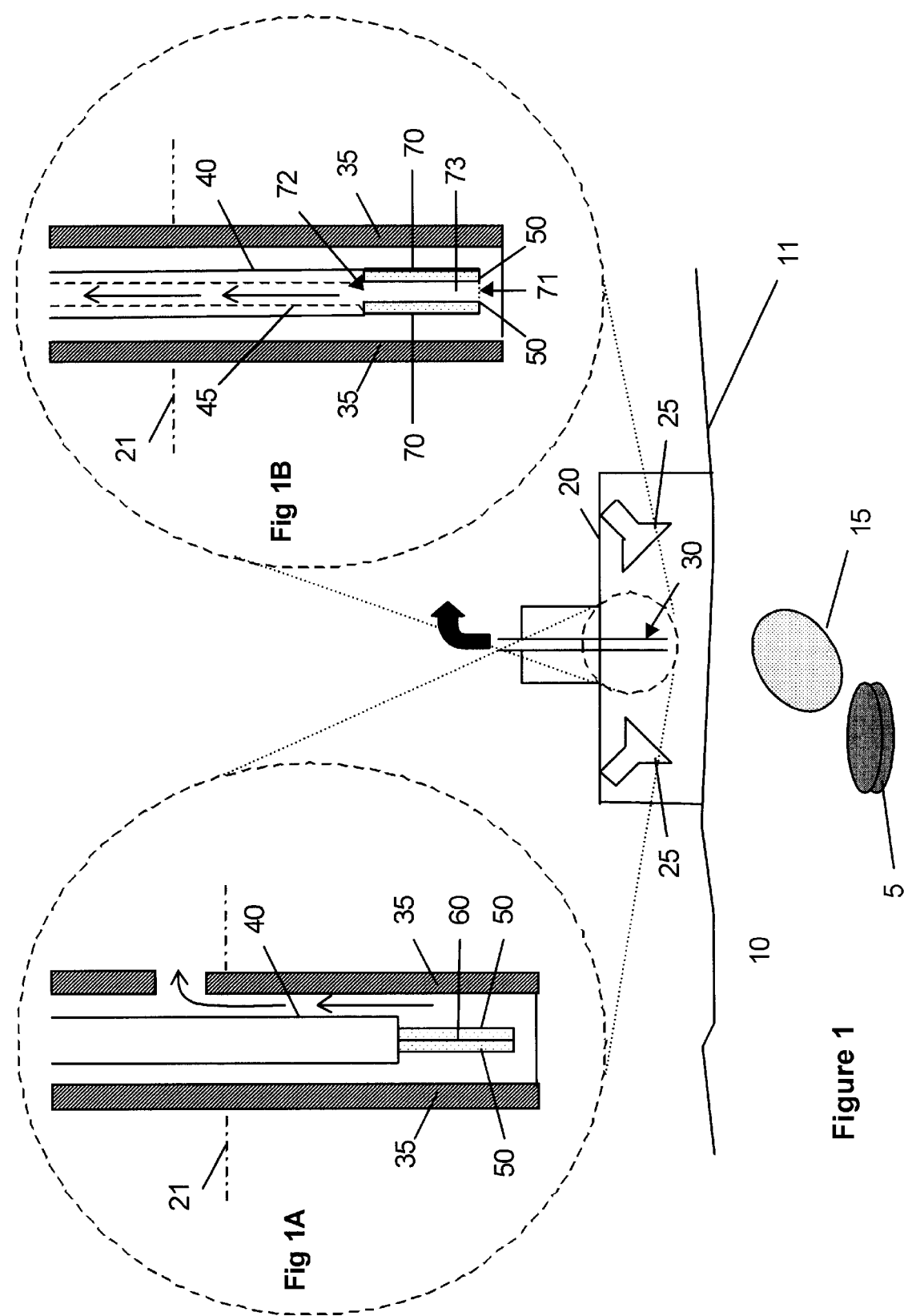
FIG. 1 is a schematic illustration of an apparatus for detecting gaseous emanations from a land mine buried in soil. Included in the figure are FIGS. 1A and FIG. 1B, expanded detail cross section depictions illustrating two approaches to employing SPME in the context of the invention.

The present invention provides a method and apparatus for improved chemical detection of target substances present in a gas. In one aspect, the invention utilizes heating, including, for example, microwave heating, to increase partitioning of target analyte so as to favor gaseous phase. In another aspect, the invention employs solid-phase microextraction using sorbent material either in a traditional passive (headspace) context, or alternatively, in an optimized, non-passive technique involving the channeling of gases. This channeling involves moving gases potentially containing one or more target substances through a tube, such as a capillary tube, in order to carry those gases into close proximity to the sorbent material. In this way, the likelihood of capturing the target chemical(s) in a short exposure time is improved versus, for example, passive headspace sampling. Two specific embodiments are described in connection with this channeling. In the first, a traditional SPME fiber coated with sorbent is used and supported within a capillary tube through which gases are channeled. In the second, the SPME fiber is omitted and replaced by a tube, such as a capillary tube, with SPME sorbent material coating the interior walls of the tube. In either of these two embodiments, the gas potentially containing target chemical (s) passes in close proximity to the sorbent material, thus improving the likelihood of capture of the target chemical(s) in a short exposure time.

The example used throughout this disclosure is that of detecting explosives in soil. A typical soil comprises a solid phase, a liquid phase (usually water) and a gas phase (usually air). Under ambient conditions, most explosives present in soil reside in a solid or liquid phase, with only a small portion partitioning into the gas phase. This low propensity to partition from the water into the air results in an extremely low Henry's law constant. The water-air partitioning is an exponential function of absolute temperature, so that by raising the temperature from ambient temperature, for example, from 25° C. to 70° C., gas partitioning increases by at least two orders of magnitude. Increasing the soil temperature by even 10° C. (above ambient) will have a favorable effect which results in availability of more target substance in the gas phase, thus increasing the likelihood of detection. Improved detection results from increasing amount of target substance in the gases to be sampled and improving the thoroughness of extraction of target substance from the carrier gas. Both of these independent parameters are addressed by the present invention.

Concerning temperature, optimized sampling can be obtained by heating soil while keeping the SPME sorbent cool. This is mentioned in the 1994 Zhang, et al., *Anal. Chem.* reference noted above. One aspect of the present invention is to accomplish heating of soil, in one embodiment, using microwaves. FIG. 1 illustrates an apparatus configuration according to an embodiment of the invention. The figure shows how microwave horns may be used in conjunction with two alternative SPME configurations to achieve the desired soil heating. The figure illustrates a landmine 5 buried in soil 10 with a plume 15, for example, containing TNT molecules. As described previously, molecules such as those in the plume 15 are likely to be present in a combination of solid and liquid phase, with only a small concentration partitioned into the gaseous (air) component of the soil in which the plume resides. Since SPME sampling according to this embodiment depends on capturing target molecules diffused into and present in gaseous soil component, it is desirable to heat the soil in order to drive more target molecules into that phase. Optimal heating temperatures will depend on a given application and the target molecules sought to be detected, however, for example, partitioning of molecules emanating from a plume containing TNT can be successfully enhanced by heating soil. Optimally, the target temperature is in the range between 80° C. and 110° C. Heating the soil to too high a temperature (or producing hot surfaces that can contact the vapor sample) may cause target chemicals to decompose or otherwise degrade thereby rendering them more difficult to detect. Insufficient heating may result in inadequate partitioning of target chemicals into the gas phase.

As illustrated in the figure, an enclosure 20 (shown with the side facing the reader cut away) is provided. The enclosure 20 can be in the form of a box positioned atop the surface 11 of the soil 10. At least one heating element, which in the illustrated embodiment is at least one microwave-generating element, is provided. The at least one heating element is capable of directing microwave radiation to and through a portion of the soil 10 beneath the enclosure 20. In the example illustrated, the at least one microwave-generating element actually comprises two microwave horns 25 directed downward toward the soil 10. It is acknowledged, however, that the appropriate number and configuration of such horns used for a given application will depend on a number of variables such as soil condition, characteristics of the target chemical substance(s) and features of the plume. Generally, though, two microwave horns will provide the desired increase in partitioning. It is also acknowledged that while microwave heating is used in the illustrated embodiment, other heating means may satisfy the objectives of the invention equally well. Advantages are apparent, though, where the heating element heats the target soil, for example, without at the same time directly heating the air surrounding the heating element or producing any surfaces hot enough to cause target chemicals to degrade. Microwave heaters or other forms of radio wave heaters are well suited for the purposes of the invention. It is noted, and discussed further below, that it is beneficial to avoid heating the sorptive surface that will be used to collect the sample. Radiant heaters, for example, may satisfactorily heat the soil causing partitioning of target chemical into gas phase. At the same time, however, they may also heat the air inside the enclosure 20 as well as the sorptive surface intended to capture target chemicals, resulting in a decrease in sample collection efficiency. In fact, it is sometimes beneficial to cool the sample-collecting element (referred to herein as a SPME assembly 30), as will be described.

Also, as illustrated in the figure, a SPME assembly 30 is provided in association with the enclosure 20. The SPME assembly 30 includes SPME sorbent positioned on a substrate according to at least two possible configurations to be described, shortly, in reference to FIGS. 1A and 1B. According to at least one embodiment, the SPME assembly 30 is in operative association with a device (not shown) for actively channeling (moving) air from within the enclosure to a region outside of the enclosure in a fashion that air passes in proximity to the SPME sorbent. The bold curved arrow in the figure depicts one possible manner in which soil gas can exit the enclosure, after passing by the SPME assembly 30, in those instances wherein gases are actively channeled. Suitable SPME sorbent materials for specific applications are known to persons skilled in the art of solid-phase microextraction, and examples of SPME compounds are described in various catalogs and other publications, including the SUPELCO™ Chromatography Products 1996 catalog (published by Supelco, Inc., Supelco Park, Bellefonte, Pa.), which is incorporated herein in its entirety.

In operation, for purposes of the illustrated embodiment, the microwave horns 25 shown in the figure direct microwave radiation generally downward into the soil 10. In so directing radiation, molecules of target chemicals present in liquid or solid phase within the plume 15 heat up and are driven into the gas phase, thereby increasing the concentration of target analyte chemical(s) in the soil gas beneath the enclosure 20. The soil gas will tend to move through the soil matrix, and a portion of the soil gas will rise with some of the soil gas entering the enclosure 20. This effect of the soil gas entering the enclosure 20 is enhanced, by some degree, as a result of the heating and also by movement of gases out of the enclosure as depicted by the bold curved arrow in the figure.

Two different SPME assembly configurations are illustrated in FIGS. 1A and 1B. The configuration shown in FIG. 1A involves using a typical SPME fiber in the inventive SPME assembly 30. Two different applications for the configuration in FIG. 1A will be described, one involving passive sample collection and the other involving active channeling of gases for enhanced sample collection. The configuration in FIG. 1B shows a SPME assembly 30 wherein SPME sorbent is supported on the inside walls of a tube rather than on a fiber. As will be described, this configuration has special applicability where active channeling of gases is used.

FIG. 1A shows a cross section of a fiber embodiment of the SPME assembly 30. The figure illustrates a central fiber 60 coated with sorbent 50. (For purposes of this disclosure including the figures, the relative thicknesses of sorbent 50 and fiber 60 are not shown to scale. Commercially available SPME fibers, exhibiting the thickness of sorbent material typically inherent in commercial SPME fibers, will adequately serve the purposes of this invention.) In the illustration, a support 40, such as a syringe plunger, holds the fiber 60. (As noted previously, a syringe can be used advantageously for convenience in later insertion of the fiber into an analysis instrument, such as a GC.)

Also shown in FIG. 1A is an insulator 35. In the illustrated embodiment, the insulator 35 is a tube, open at the bottom, surrounding the fiber 60 supporting the sorbent 50. The function of the insulator 35 is to prevent the SPME fiber from heating significantly (or at all) as a consequence of the operation of the heater used to elevate the temperature within the soil. (In the illustrated case microwave horns 25 are used, in which instance significant direct heating of air inside the enclosure 20 is largely averted. However, insulation and/or cooling of the SPME element 30 can be advantageous even where microwave or other radio wave heating means is employed. Certainly, advantage is obtained in using an insulator where other forms of heater, for example a radiant heating apparatus, are used which may tend to heat the air inside the enclosure.) The sorbent collects sample most effectively when maintained at ambient temperature, or even below, depending on the sorbent used and the circumstances of sampling. Where cooling is desired, the insulator tube 35 can be replaced with another form of tube or equivalent enclosing structure capable of being actively cooled, such as by electrical or other means known in the cooling art. Suitable coolers can include (but are not limited to): Peltier cooling, gaseous cooling such as the $CO_2$ method described in U.S. Pat. No. 5,496,741 (Pawliszyn, J. B.) and other circulating liquid or gas coolers.

The configuration in FIG. 1A can serve either to optimize passive headspace sampling, or alternatively, to benefit from active channeling of gases. Even where no effort is made to actively move gases past the SPME fiber, improved sample collection is obtained over previous art as a result of the heating of the soil (to increase partitioning) and using the enclosure 20 (to provide a degree of concentration). Heating, as illustrated, may be accomplished through use of the microwave horns 25 and the enclosure 20.

FIG. 1A also shows an example of how active channeling of the gases past the SPME fiber could take place consistent with the principles of the invention, thereby increasing the likelihood of capture of target substances by the SPME sorbent. In the illustrated case, gases may be caused to flow past the SPME fiber, for example, by being drawn through the insulator tube 35 in the direction shown by the finely printed arrows. In the illustrated example, gases are allowed to exhaust through an opening in the tube, however, any exhaust means enabling the flow of gases past the SPME fiber would satisfy the ends of the invention.

As discussed, in operation the apparatus may also include a device for moving air from within the enclosure 20 so that it passes in proximity to the SPME fiber and then out of the enclosure 20 as illustrated by the bold arrow in FIG. 1. The air-moving device, not shown in the figure, can include any of the various pumps, fans and other air moving devices that are well known in the art. It is possible for the invention to operate successfully without such an air moving device, with gases simply diffusing throughout the enclosure 20, including in proximity to the SPME fiber, however, as noted above, passive collection can be very slow. Accordingly, for purposes of the present invention, it may be desirable to actively move gases toward and in proximity to the SPME fiber. Also shown in the Figure is the ceiling 21 of the enclosure to clearly illustrate that the tube 35 penetrates the enclosure and permits passage of gases from within the enclosure 20 to a region outside of the enclosure.

By actively moving gases from the enclosure, through the tube, and in proximity to the fiber, diffusion distances are minimized and the likelihood of target analytes being captured by the sorbent material 50 on the fiber is increased.

FIG. 1B shows different embodiment employing a novel SPME configuration that does not use the traditional SPME fiber. In this instance, rather than a fiber, a SPME capillary is provided. The SPME capillary comprises a tube, such as a capillary tube 70, including two open ends 71 and 72, and a central channel 73. Sorbent 50 coats the inside of the capillary tube 70 and, specifically, the surface bounding the channel 73, as depicted in the figure. (As in the previously described embodiment, the relative thicknesses of the sorbent 50 as compared with the other illustrated elements including the walls of the tube 70 are not shown to actual scale. Appropriate actual thicknesses of sorbent material will depend on the particular sorbent material deployed, however, such thicknesses will be similar to those used for commercial SMPE fibers with similar sorbents.) In this instance, also, an air-moving device is necessary in order for the capillary tube embodiment to function optimally. As with the previously described embodiment, various air moving devices including suction, fans and pumps are well known and could be successfully adapted to satisfy purposes of the present invention.

FIG. 1B shows a support member 40 supporting the SPME capillary (comprising the capillary tube 70 and the sorbent 50). Functional tubes 70 include tubes ranging in size from 0.75 mm to 7.5 mm ID, however, depending on a particular application, larger or smaller tubes may be suitable. FIG. 1B also illustrates a conduit 45 is depicted within the support member 40. As noted, the capillary tube 70 includes two open ends. The first open end 71 is open to the interior of the enclosure 20 and the second open end 72 adjoins the support member 40 so that the central channel 73 of the capillary tube 70 substantially aligns with the conduit 45 of the support member 40.

During collection of sample using the configuration illustrated in FIG. 1B, air movement means is applied so that gases (including carrier gas with perhaps entrained target analytes) are drawn into and through the capillary tube 70. In particular, gases pass via the first open end 71 of the capillary tube 70, through the capillary tube central channel 73, and thereby past the sorbent 50 lining the interior surface of the capillary tube 70. The gases then pass out of the capillary tube central channel 73, through the second open end 72 of the capillary tube 70 and then into the conduit 45 (or other equivalent structure through which gases can pass). The finely printed arrows in FIG. 1B illustrate the direction of channeled flow of gases in this embodiment. As a result of the channeled flow of gases just described, recovery of analytes from carrier gas is enhanced versus a technique that employs passive diffusion. Likewise, the time for equilibration is minimized since the gases (for example, soil gas) are drawn in close proximity to the SPME sorbent 50. The distance of gas phase diffusion is reduced as compared with traditional headspace SPME techniques using traditional SPME fibers. Again, as before, also shown in the Figure is the ceiling 21 of the enclosure to clearly illustrate that the conduit 45 penetrates the enclosure and permits passage of gases from within the enclosure 20 to a region outside of the enclosure.

It is noted that although the desorption approach described for traditional SPME fibers, whereby fibers can be injected into a GC inlet, has been standardized, desorption of target chemicals from the inventive SPME capillary may require additional steps. These include using known and commonly used thermal desorption techniques combined with, for example, causing a purge flow of gas through the SPME capillary in order to carry desorbed target chemicals into the GC inlet.

The invention being thus described, it will be obvious that the same may be varied in many ways. Such variations are not to be regarded as a departure from the spirit and scope of the invention, and all such modifications as would be obvious to one skilled in the art are intended to be included within the scope of the appended claims. It is intended that the scope of the invention be defined by the claims appended hereto. The entire disclosures of all references, applications, patents and publications cited above are hereby incorporated by reference.

We claim:

1. An apparatus for capturing chemical substances in a carrier gas comprising:

a tube including an inner surface, first and second open ends, and a channel therebetween, the channel bound by the inner surface of the tube, sorbent material affixed to the inner surface of the tube, temperature regulation means selected from the group consisting of thermal insulation at least partially enclosing the tube and cooling means in operative association with the tube which, when activated, causes the sorbent material to attain a temperature lower than that of ambient air outside of the tube, gas moving means for moving the carrier gas through the channel, and a partially enclosed structure including:

an interior region, support holding the tube so that when the gas moving means is actuated, gases move from the interior region of the partially enclosed structure, through the channel of the tube and away from the partially enclosed structure, and an opening in the partially enclosed structure adapted to communicate with a soil region having a surface so that gases emanating from the surface of the soil region can pass into the interior region of the partially enclosed structure.

2. The method of claim 1 further comprising at least one heater.

3. The method of claim 2 wherein the at least one heater is selected from the group consisting of microwave heaters and radio wave heaters.

4. An apparatus for capturing chemical substances in a carrier gas comprising:

a tube including an inner surface, first and second open ends, and a channel therebetween, the channel bound by the inner surface of the tube, sorbent material affixed to the inner surface of the tube, gas moving means for moving the carrier gas through the channel, a partially enclosed structure including an interior region support holding the tube so that when the gas moving means is actuated, gases move from the interior region of the partially enclosed structure, through the channel of the tube and away from the partially enclosed structure, and an opening in the partially enclosed structure adapted to communicate with a soil region having a surface so that gases emanating from the surface of the soil region can pass into the interior region of the partially enclosed structure, at least one heater selected from the group consisting of microwave heaters and radio wave heaters, and thermal insulation at least partially enclosing the tube.

5. The apparatus of claim 4 further comprising cooling means in operative association with the tube whereby, when activated, the cooling means causes the sorbent material to attain a temperature lower than that of ambient air outside of the tube but otherwise within the interior region of the partially enclosed structure.

6. An apparatus for use in conjunction with detecting presence of explosive material in soil, the apparatus comprising:
- a partially enclosed structure including:
  - an interior region,
  - an opening adapted to communicate with a soil region having a surface so that gases emanating from the surface of the soil region can pass into the interior region of the partially enclosed structure, and
  - supported in the partially enclosed structure, a fixture including sorbent capable of sorbing substances present in soil gas due to presence of explosive material in soil containing such soil gas, and the fixture further including temperature regulation means selected from the group consisting of thermal insulation at least partially enclosing the sorbent and cooling means in operative association with the sorbent which, when activated, causes the sorbent to attain a temperature lower than that of ambient air in the partially enclosed structure.

7. The apparatus of claim 6 wherein the fixture including sorbent is selected from the group consisting of
- a solid-phase microextraction fiber,
- a solid-phase microextraction fiber supported within a capillary tube associated with gas-moving means capable of drawing gases from the interior region through the capillary tube, and
- a capillary tube operatively associated with gas-moving means capable of drawing gases from the interior region through the capillary tube, the capillary tube including an inner surface with sorbent material supported thereon.

8. The apparatus of claim 7 further comprising heating means capable of heating at least part of the soil to a temperature to at least 10° C. above ambient temperature of said part of the soil immediately prior to said heating.

9. The apparatus of claim 8 wherein the heating means is selected from the group consisting of microwave heaters and radio wave heaters.

* * * * *